United States Patent [19]

Failli et al.

[11] 4,351,828
[45] Sep. 28, 1982

[54] N-SUBSTITUTED CYCLOPEPTIDE DERIVATIVES

[75] Inventors: Amedeo Failli, St. Laurent; Hans U. Immer, Mount Royal; Manfred K. Götz, Hudson, all of Canada

[73] Assignee: American Home Products Corporation, New York, N.Y.

[21] Appl. No.: 164,663

[22] Filed: Jun. 30, 1980

Related U.S. Application Data

[62] Division of Ser. No. 941,827, Sep. 11, 1978, Pat. No. 4,237,045.

[51] Int. Cl.³ ............................................. A61K 37/00
[52] U.S. Cl. ............................ 424/177; 260/112.5 R; 424/14; 424/357
[58] Field of Search .................. 424/177; 260/112.5 R

[56] References Cited

PUBLICATIONS

Degering, Organic Chemistry, 1951, pp. 145–147, 151 and 152.
Synthetic Org. Chem.; 5/1953, pp. 412–415, 605 and 813.
Organic Chemistry, 1956, 2nd Ed., pp. 413–416.

Primary Examiner—Dale R. Ore
Attorney, Agent, or Firm—Arthur E. Wilfond

[57] ABSTRACT

The N-substituted cyclopeptide derivatives of formula I

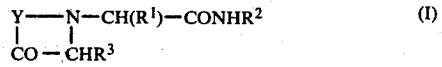

in which $R^1$ is lower alkyl, $R^2$ is lower alkyl or cyclo(-lower)alkyl, $R^3$ is a neutral amino acid side chain and Y is a peptide residue having three to nine amino acid residues and a method for the preparation of the compounds of formula I are disclosed. The compounds of formula I are useful antibacterial and antifungal agents. Pharmaceutical compositions also are disclosed.

7 Claims, No Drawings

N-SUBSTITUTED CYCLOPEPTIDE DERIVATIVES

This is a division of application Ser. No. 941,827 filed Sept. 11, 1978, now U.S. Pat. No. 4,237,045.

BACKGROUND OF THE INVENTION (a) Field of Invention

The present invention relates to N-substituted cyclopeptide derivatives with antibacterial and antifungal activity and to a process for their preparation.

(b) Description of the Prior Art

A number of cyclic peptides have been either isolated from natural sources or prepared by classical synthetic methods, for example, see the review by E. Schröder and K. L. Lüoke, "The Peptides;" Vol. II; Academic Press, New York, 1966, pp 424–478.

The present invention discloses novel cyclopeptide derivatives in which a nitrogen atom of the peptide back bone is substituted. These compounds have been found to have the desirable attributes of useful microbial activity coupled with a low order of toxicity.

In addition, a novel process for preparing N-substituted cyclopeptides is disclosed.

SUMMARY OF THE INVENTION

The N-substituted cyclopeptide derivatives of this invention are represented by the compounds of formula I:

(I)

in which $R^1$ is lower alkyl, $R^2$ is lower alkyl or cyclo(lower)alkyl, $R^3$ is a neutral amino acid side chain and Y is a peptide residue having three to nine neutral amino acid residues.

A preferred group of N-substituted cyclopeptide derivatives of this invention are represented by the compounds of formula I in which $R^1$ is lower alkyl, $R^2$ is lower alkyl or cyclo(lower)alkyl, $R^3$ is a neutral amino acid side chain selected from hydrogen or lower alkyl and Y is a peptide residue having five neutral amino acid residues.

Another preferred group of N-substituted cyclopeptide derivatives of this invention are represented by the compounds of formula I in which $R^1$ is lower alkyl; $R^2$ is cyclo(lower)alkyl; $R^3$ is a neutral amino acid side chain selected from hydrogen or lower alkyl and Y is a peptide residue of the formula NHCH($R^4$)CO—NHCH($R^5$)CO—NHCH($R^6$)CO—NHCH($R^7$)CO—NHCH($R^8$)CO wherein $R^4$ is hydrogen, lower alkyl or benzyl; $R^5$, $R^6$ and $R^7$ each independently is hydrogen or lower alky; and $R^8$ is hydrogen, lower alkyl or 2-(methylthio)ethyl.

Still another preferred group N-substituted cyclopeptide derivatives of this invention are represented by the compounds of formula I in which $R^1$, $R^2$ and $R^3$ are as defined immediately above and Y is a peptide residue of the formula NHCH—($R^4$)CO—NHCH($R^5$)CO—NHCH($R^6$)CO—NHCH($R^7$)CO—NHCH($R^8$)CO wherein $R^4$ is hydrogen or benzyl; $R^5$, $R^6$ and $R^7$ each independently is hydrogen or lower alkyl; and $R^8$ is hydrogen or 2-(methylthio)ethyl.

The compounds of formula I in which $R^1$, $R^2$, $R^3$ and Y are as defined herein are prepared by a process which comprises condensing together an aldehyde of formula $R^1$CHO in which $R^1$ is as defined herein, an isonitrile of formula $R^2$NC in which $R^2$ is as defined herein and a peptide of formula $H_2N$—CH($R^3$)—CO—Y—OH in which $R^3$ and Y are as defined herein.

The compounds of formula I form a pharmaceutical composition which comprises a compound of formula I and a pharmaceutically acceptable carrier.

The compounds of formula I are useful for treating bacterial and fungal infections in a mammal by administering to the mammal an antibacterial and antifungal effective amount of a compound of formula I.

DETAILS OF THE INVENTION

The term "lower alkyl" as used herein means straight chain alkyl radicals containing from one to six carbon atoms and branched chain alkyl radicals containing three or four carbon atoms and includes methyl, ethyl, propyl, isopropyl, butyl, isobutyl, pentyl, hexyl and the like.

The term "cyclo(lower)alkyl" as used herein means saturated cyclic hydrocarbon radicals containing from three to six carbon atoms and includes cyclopropyl, cyclobutyl, cyclopentyl and cyclohexyl.

The term "organic proton acceptor" as used herein includes triethylamine, N-ethylmorpholine, N-ethyldiisopropylamine and the like.

The terms "amino acid" and "amino acid residue" as used herein means the common amino acids and amino acid residues having a neutral side chain and includes alanine, asparagine, cysteine, glycine, tryptophan, methionine, serine, tyrosine, valine, leucine, phenylalanine, isoleucine, proline, threonine and the like.

In general the abbreviations used herein for designating the amino acids and the protective groups are based on recommendations of the IUPAC-IUB Commission on Biochemical Nomenclature, see Biochemistry, 11, 1732(1972). For instance Ala, Leu and Gly represent "residues" of L-alanine, L-leucine and glycine, respectively. The term "residue" means a radical derived from the corresponding L-amino acid by eliminating the hydroxy portion of the carboxy group and a hydrogen of the α-amino group. The term "amino acid side chain" is that part of a common neutral amino acid exclusive of the —CH($NH_2$)COOH portion, as defined by K. D. Kopple, "Peptides and Amino Acids," W. A. Benjamin Inc., New York and Amsterdam, 1966, pages 2 and 33. Examples of neutral amino acid side chains are —$CH_2CH(CH_3)_2$ (the side chain of leucine), —H(glycine), —$CH_3$(alanine), —$CH_2CONH_2$(asparagine), —$CH_2SH$(cysteine), 3-indolylmethylene(tryptophan), —$CH_2CH_2SCH_3$(methionine), —$CH_2OH$(serine), 4-hydroxybenzyl(tyrosine), —CH($CH_3$)(valine), benzyl(phenylalanine), —CH($CH_3$)$C_2H_5$ (isoleucine), —CH(OH)$CH_3$(threonine) and the like. Note, therefore, that the term "amino acid side chain" includes hydrogen.

The amino acids and amino acid residues are all of the L configuration. It will be noted that the structures of the compounds of this invention include asymmetric carbon atoms. It is to be understood accordingly that the isomers arising from such asymmetry are included within the scope of this invention. Such isomers are obtained in substantially pure form by classical separation techniques and by sterically controlled synthesis and have arbitrarily been named as isomers L or M, respectively.

A number of procedures or techniques for the preparation of peptides have hitherto been well established and found in general textbooks of peptide chemistry; for example K. D. Kopple, supra, pp. 33–51 and E. Schröder and K. L. Lüoke, "The Peptides;" Vol. 1; Academic Press, New York, 1965, pp. 3–128. For instance, the functional groups which are not involved in the peptide bond formation reaction are optionally protected by a protecting group or groups prior to the condensation reaction. Examples of protecting groups for an amino function of a peptide or amino acid not involved in the peptide bond formation are: the alkoxycarbonyls which include benzyloxycarbonyl (represented by Z), t-butoxycarbonyl (represented by Boc), α,α-dimethyl-3,5-dimethoxybenzyloxycarbonyl (represented by Ddz), 2-(p-biphenyl)-isopropyloxycarbonyl (represented by Bpoc), p-chlorobenzyloxycarbonyl, p-methoxybenzyloxycarbonyl, isopropyloxycarbonyl, or ethoxycarbonyl; the acyl type protecting groups which include formyl, trifluoroacetyl, phthalyl, acetyl (Ac), or toluenesulfonyl; the alkyl type protecting groups which include triphenylmethyl or trityl (represented by Trt) or benzyl; the preferred protecting groups used in the process of this invention are benzyloxycarbonyl, t-butoxycarbonyl, triphenylmethyl and α,α-dimethyl-3,5-dimethoxy-benzyloxycarbonyl. The carboxylic acid function of a peptide or amino acid can be considered protected by a lower alkyl or lower aralkyl ester which includes methyl (represented by OMe), ethyl (OEt), benzyl (OBzl) or tert-butyl (OBu$^t$) esters.

A peptide or amino acid is coupled with another peptide or amino acid to form a new peptide by the elimination of water (i.e. dehydrative coupling). More specifically, the OH portion of a free carboxyl group of a peptide or amino acid and the H portion of a free amino group of a peptide or amino acid are eliminated to form a new amide bond joining the peptide or amino acid starting materials. To promote facile condensation of a peptide free carboxyl group with a free amino group of another peptide to form a new peptide bond, the free carboxyl group must be activated. Descriptions of such carboxyl activating groups are included in the general textbooks of peptide chemistry by Kopple, or Schröder and Lüoke, cited above. Examples of the activated form of a carboxyl are acid chloride, anhydride, azide, imidazolide, activated ester or O-acyl urea of a dialkylcarbodiimide (i.e. cyclohexylcarbodiimide). The following activated esters have proved to be particularly suitable in the process of this invention: 2,4,5-trichlorophenyl (represented by OTcp), pentachlorophenyl (OPcp), p-nitrophenyl(ONp), or 1-benzotriazolyl; the succinimido derivative also is useful for this purpose.

The coupling of a peptide or amino acid having the activated carboxyl with the peptide or amino acid having a free amino group is conducted in an inert organic solvent at a temperature from −30° C. to about 50° C. For coupling to occur, the amino group must not be protonated. A sufficient amount of an organic proton acceptor is added to the above reaction mixture until the amino group is no longer protonated (usually pH 7.2 to 8.0).

The terms "peptide, dipeptide, tripeptide, and the like" used herein are not limited to refer to the respective parent peptides but also are used in reference to modified peptides which are functionalized or having protecting groups. The term "peptide" as used herein can be used in reference to a peptide with one to nine amino acid residues.

ANTIBACTERIAL AND ANTIFUNGAL ACTIVITY

The 4,1-benzoxazonine derivatives of this invention exhibit utility as antibacterial agents against a number of pathogenic bacteria, for example, *Klebsiella pneumoniae* and *Serratia marcescens*, and as antifungal agents against a number of pathogenic fungi, for example, *Candida albicans*, *Microsporum gypseum* and *Trichophyton granulosum*, in standard tests for antibacterial and antifungal activity, such as those described in "Antiseptics, Disinfectants, Fungicides and Sterilization," G. F. Reddish, Ed., 2nd ed., Lea and Febiger, Philadelphia, 1957 or by D. C. Grove and W. A. Randall in "Assay Methods of Antibiotics," Med. Encycl. Inc., New York, 1955.

For example, by employing a test like the serial broth dilution, see Grove and Randall, cited above, in which dilutions of the compounds of this invention in nutrient broth are inoculated with the microorganisms or fungi, described above, incubated at 37° C. for 2 days, respectively, and examined for the presence of growth, it may be shown that isomers L and M of cyclo[N-(1-(1-methylethyl)-2-cyclohexylamino-2-oxo-ethyl]-alanyl-phenylalanyl-valyl-glycyl-leucyl-methionyl] (described in Example 2) are able to inhibit growth totally in this system of *Klebsiella pneumoniae* and *Serratia marcescens* at a concentration of 100/mcg/ml.

When the compounds of this invention are employed as antimicrobial antibacterial or antifungal agents in a mammal they are administered alone or in combination with pharmacologically acceptable carriers. The amount of the compound is determined by the solubility and chemical nature of the compound, chosen route of administration and standard biological practice. For example, the compounds may be administered orally in solid form containing such excipients as starch, milk sugar, certain types of clay and so forth. They may also be administered orally in the form of solutions or they may be injected parenterally. For parenteral administration they may be used in the form of a sterile solution containing other solutes, for example, enough saline or glucose to make the solution isotonic.

The dosage of the present therapeutic agents as antibacterial or antifungal agents will vary with the form of administration and the particular compound chosen. Furthermore, it will vary with the particular host under treatment. Generally, treatment is initiated with small dosages substantially less than the optimum dose of the compound. Thereafter, the dosage is increased by small increments until the optimum effect under the circumstances is reached. In general, the compounds of this invention are most desirably administered at a concentration level that will generally afford antimicrobial effective results without causing any harmful or deleterious side effects and preferably at a level that is in a range of from about 1.0 mg to about 500 mg per kilogram body weight per day, although as aforementioned variations will occur. However, a dosage level that is in the range of from about 10 mg to about 200 mg per kilogram body weight per day is most desirably employed in order to achieve effective results.

In addition, the compounds may be employed topically. For topical application they may be formulated in the form of solutions, creams, or lotions in pharmaceutically acceptable vehicles containing 0.1–5 percent, preferably 2 percent, of the agent and may be administered topically to the infected area of the skin.

Also the antibacterial properties of the compounds of this invention may be utilized for washing equipment in hospitals, homes and farms, instruments used in medicine and bacteriology, clothing used in bacteriological laboratories, and floors, walls and ceiling in rooms in which a background free of bacteria is desired. When employed in this manner the compounds of this invention may be formulated in a number of compositions comprising the active compound and an inert material. In such compositions, while the compounds of formula I of this invention may be employed in concentrations as low as 500 p.p.m., from a practical point of view, it is desirable to use from about 0.10 percent by weight, to about 5 percent by weight or more.

The formulations that may be used for antiseptic wash solutions of the compounds of this invention are varied and may readily be prepared by standard techniques, see for example, "Remington's Practice of Pharmacy," E. W. Martin, et al., Eds., 12th ed., Mack Publishing Company, Easton, Pa., 1961, pp. 1,121–1,150. In general, the compounds may be made up in stock solutions. They can also be formulated as suspensions in an aqueous vehicle. These make useful mixtures for decontaminating premises. Also, aqueous vehicles containing emulsifying agents, such as sodium lauryl sulfate, and relatively high concentrations, e.g., up to about 5 percent by weight, of the compounds may be formulated by conventional techniques.

A typical antiseptic preparation useful for disinfecting floors, walls, ceiling, and articles in a contaminated room may be prepared by adding 5 to 25 g of a compound of this invention to a mixture of 150 to 300 g of polyethylene glycol 1,540 and 150 to 300 g of polyethylene glycol 300. The resulting mixture is stirred while a solution of 1 to 10 g of sodium lauryl sulfate in 300 to 400 ml of water is added portionwise. The article to be disinfected is coated or immersed in the preparation for a prolonged time, for example, one hour, and then rinsed with sterile water.

PROCESS

The starting materials required for the preparation of the compounds of formula I are aldehydes, isonitriles and peptides. These starting materials are either known or commercially available.

The aldehydes of formula $R^1CHO$ are known and most are commercially available, for example, isobutyraldehyde and benzaldehyde, or are prepared by known methods, for example, see P. Karrer, "Organic Chemistry," 2nd. ed., Elsevier Publishing Co. Inc., New York, 1946, p. 149.

The isonitriles of formula $R^2NC$, are either known, namely, ethyl isocyanoacetate is described by R. Appel et al., Angew. Chem. Int. ed., 10 132(1971) or are easily prepared by known methods, for example, by the methods described by P. Hoffmann, et al. in "Isonitrile Chemistry," Organic Chemistry, Vol. 20, I. Ugi Ed., Academic Press, New York, 1971. p.9.

The peptides of formula $H_2N—CH(R^3)—CO—Y—OH$ are either known or commercially available, for example, glycyl-glycyl-glycine, or are prepared by known methods used in peptide chemistry.

The compounds of this invention are prepared by the following description of a preferred embodiment.

The practice of the preferred embodiment of the process of this invention involves the condensation of the following three starting materials; (1) an aldehyde of formula $R^1CHO$ in which $R^1$ is lower alkyl, (2) an isonitrile of formula $R^2NC$ in which $R^2$ is lower alkyl or cyclo(lower)alkyl, and (3) a peptide of formula $H_2N—CH(R^3)—CO—Y—OH$ in which $R^3$ is an amino acid side chain and Y is a peptide residue having three to nine amino acid residues to obtain the corresponding compound of formula I:

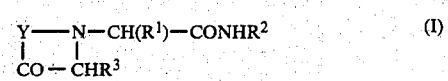

in which $R^1$, $R^2$, $R^3$ and Y are as defined herein.

Although not critical, it is preferable to use approximately equimolar amounts of the isonitrile of formula $R^2NC$ and the peptide of formula $H_2N—CH(R^3)—CO—Y—OH$ and about one to five molar equivalents, preferably two to four molar equivalents, of the aldehyde of formula $R^1CHO$ for this condensation. The condensation is effected most conveniently in a dry inert organic solvent, for example, dimethylformamide, dimethyl sulfoxide or in an aliphatic alkanol which includes methanol, ethanol, ethylene glycol, 1,2-propanediol and the like. The preferred inert organic solvent can be selected from dimethylformamide, dimethyl sulfoxide or mixtures thereof.

The temperature and duration of the condensation are also not critical. The reaction may be performed at temperatures ranging from $-20°$ to $100°$ C.; however, a range from $10°$ to $40°$ C. is most convenient. The reaction time can be varied, and depends on the reactivity of the various starting materials; however, reaction times from one hour to several days are employed generally, with ten hours to ten days being preferred.

The above condensation of the three starting materials requires the use of dilute solutions to counteract undesirable polymerization. Suitable and preferred concentrations of the reaction solution with respect to the isonitrile or peptide starting materials can range from 0.1 mmole per ml of solvent to 1.0 mmole per ml of solvent.

Some of the peptides of formula $H_2N—CH(R^3)—CO—Y—OH$ may not be sufficiently soluble in the inert organic solvent selected for the condensation to give the corresponding compound of formula I in sufficient yield. A useful method to increase the solubility of the peptide starting material is to prepare the acid addition salt of the peptide starting material, for example, salts formed with one molar equivalent of hydrochloric acid or trifluoroacetic acid. The acid addition salt of the peptide starting material is employed in the condensation along with a corresponding amount of an organic proton acceptor, for example, triethylamine, N-methyl morpholine and the like.

Thereafter, the compound of formula I is isolated and purified according to standard procedures. For instance the product can be precipitated with a di(lower)alkyl ether or water and, if needed, purified by chromatography and crystallization.

It should be noted that the product formed is a mixture of two isomers. Separation of the isomers can be effected by chromatography. For example, chromatography using silica gel as the absorbent has been found to be effective for this separation.

The following example illustrate further this invention.

EXAMPLE 1

Alanyl-phenylalanyl-valyl-glycyl-leucyl-methionine Trifluoroacetate

A solution of valyl-glycine ester hydrochloride [7.14 g, described by N. Metsuyasu et al., Mem. Fac. Sci. Kyushu Univ., Ser. C, 7, 63(1970)] and triethylamine (3.03 g) in dry dimethylformamide (65 ml) is stirred at 0° to 5° C. for 10 minutes and filtered. A solution of t-butoxycarbonyl-phenylalanine p-nitrophenyl ester [11.6 g, described by K. Hofmann et al., J. Am. Chem. Soc. 87, 620(1965)] in dry dimethylformamide (33 ml) at 0° C. is added to the filtrate. The mixture is stirred at 0° C. for 3 days and added to a mixture of ice and water. The precipitate is collected, dried and crystallized from methanol-diisopropyl ether to give t-butoxycarbonyl-phenylalanyl-valyl-glycine ethyl ester, mp 160°–162° C.

A solution of the latter compound (11.2 g) and trifluoroacetic acid (48 ml) is stirred at 0° C. for 20 minutes and at 25° C. for 10 minutes. The solution is evaporated to give a residue of phenylalanyl-valyl-glycine ethyl ester trifluoroacetate.

A solution of the latter compound (14.3 g) and triethylamine (35 ml) in dimethylformamide (45 ml) is stirred at 0° C. for 5 minutes and a solution at 0° C. of t-butoxycarbonyl alanine 2,4,5-trichlorophenyl ester [9.2 g, described by W. Broadbent et al., J. Chem. Soc. (C), 2602(1967)] in dimethylformamide (59 ml) is added. The solution is stirred at 0° C. for 24 hours and poured into a mixture of water and ice. The precipitate is collected, dried and crystallized from methanol-diisopropyl ethyl to give t-butoxycarbonylalanyl-phenylalanyl-valyl-glycine ethyl ester, mp 207°–203.5° C.

To a stirring suspension of the latter compound (10.4 g) in methanol-2-methoxyethanol (1:1, 114 ml) at 0° C. is added dropwise 1 N sodium hydroxide (24.4 ml) over 15 minutes.

The mixture is stirred at 25° C. for 2 hours and added to a mixture of water and ice. The aqueous solution is acidified with 1 N hydrochloric acid (24.4 ml) and acetic acid (15 drops). The precipitate is collected, washed with water and dried to give t-butoxycarbonyl-alanyl-phenylalanyl-valyl-glycine, mp 250°–260° C. (dec.).

A solution of the latter compound (2.62 g) and carbonyldiimidazole (0.862 g) in anhydrous dimethylformamide (10 ml) is stirred at −15° C. for 30 minutes and a solution of leucyl-methionine methyl ester trifluoroacetate [2.08 g, prepared by reacting t-butoxycarbonyl-leucyl-methionine methyl ester, described by K. Lübke et al., Justus Liebigs' Ann. Chem., 679, 195 (1964) with trifluoroacetic acid] and triethylamine (0.8 ml) is dimethylformamide (10 ml) is added. The reaction mixture is stirred at 25° C. for 20 hours and evaporated. The residue is washed with 5% aqueous sodium bicarbonate solution and water and dried to give t-butoxycarbonyl-alanyl-phenylalanyl-valyl-glycyl-leucyl-methionine methyl ester, mp 252°–254° C.

A mixture of the latter compound (3.65 g) in hot 2-methoxyethanolmethanol (1:1, 194 ml) is added to cold water (25 ml) and the aqueous is cooled to 5° C. Sodium hydroxide (1 N, 9.72 ml) is added. The solution is stirred at 25° C. for 24 hours and added to a mixture of ice-brine (98 ml), 1 N hydrochloric acid (10.7 ml) and acetic acid (5 drops). The precipitate is collected, washed with cold water, dried and crystallized from methanol-water to give crystals of t-butoxycarbonyl-alanyl-phenylalanyl-valyl-glycyl-leucyl-methionine, mp 252°–281° C.

A solution of the latter compound (4.14 g) in trifluoroacetic acid (16.5 ml) is stirred at 0° C. for 30 minutes and at 25° C. for 45 minutes and evaporated. The residue is triturated with diethyl ether to give the title compound, mp 260°–263° C.

EXAMPLE 2

Cyclo[N-[1-(1-methylethyl)-2-cyclohexylamino-2-oxo-ethyl]-alanyl-phenylalanyl-valyl-glycyl-leucyl-methionyl] (1; $R^1$=CH(CH$_3$)$_2$, $R^2$=cyclohexyl, $R^3$=CH$_3$ and Y=Phe-Val-Gly-Leu-Met)

A solution of alanyl-phenylalanyl-valyl-glycyl-leucyl-methionine trifluoroacetate (2.14 g, described in Example 1) in dry dimethylformamide (36.5 ml) is added over 5.5 hours to a solution of 2-methylpropanal (0.684 g), cyclohexylisonitrile (0.314 g) and triethylamine (0.288 g) in dry dimethylformamide (7 ml). Pyridine is added to bring the solution to pH 7.0. The solution is stirred at 25° C. for 65 hours and evaporated. The residue is subjected to chromatography on silica gel using benzene-isopropanol (95:5) and the initial eluant fractions are evaporated to give isomer L of the title compound, $[\alpha]_D^{25}$ −182° (c=1, dimethylformamide). The latter eluant fractions are evaporated to give isomer M of the title compound $[\alpha]_D^{25}$ −77° (c=1, dimethylformamide).

In the same manner but replacing 2-methylpropanal with an equivalent amount of acetaldehyde, hexanal or 3-methylbutanal, the following compounds of formula I are obtained, respectively: cyclo[N-(1-methyl-2-cyclohexylamino-2-oxo-ethyl)-alanylphenylalanyl-valyl-glycyl-leucyl-methionyl] and cyclo[N-[1-(2-methylpropyl)-2-cyclohexylamino-2-oxo-ethyl]-alanyl-phenylalanyl-valyl-glycyl-leucyl-methionyl].

In the same manner but replacing cyclohexylisonitrile with an equivalent amount of cyclobutylisonitrile, ethylisonitrile or pentylisonitrile, the following compounds of formula I are obtained, respectively: cyclo[N-[1-(1-methylethyl)-2-cyclobutylamino-2-oxo-ethyl]-alanyl-phenylalanyl-valyl-glycyl-leucyl-methionyl], cyclo[N-[1-(1-methylethyl)-2-ethylamino-2-oxo-ethyl]-alanyl-phenylalanyl-valyl-glycyl-leucyl-methionyl] and cyclo[N-[1-(1-methylethyl)-2-pentylamino-2-oxo-ethyl]-alanyl-phenylalanyl-valyl-glycyl-leucyl-methionyl].

EXAMPLE 3

Cyclo[N-[1-(-methylethyl)-2-cyclohexylamino-2-oxo-ethyl]-glycyl-glycyl-glycyl-glycyl-glycyl-glycyl](I; $R^1$=CH(CH$_3$)$_2$, $R^2$=cyclohexyl, $R^3$=H and Y=Gly-Gly-Gly-Gly-Gly)

A solution of glycyl-glycyl-glycyl-glycyl-glycyl-glycine trifluoroacetate [5.98 g, prepared by reacting trifluoroacetic acid with glycyl-glycyl-glycyl-glycyl-glycyl-glycine described by E. Fisher, Chem. Ber., 39, 453(1906)] in dimethyl sulfoxide (25 ml) is added over 8 hours to a solution of 2-methylpropanal (3.1 g), cyclohexylisocyanide (1.39 g) and triethylamine (1.26 g) in dimethyl sulfoxide (10 ml). Pyridine is added until the solution is pH 7 and the solution is stirred at 25° C. for 6 days. The solution is evaporated and the residue is subjected to chromatography on silica gel using chloroform-methanol (90:10). The eluate is evaporated and the residue is crystallized from methanol-chloroform-acetone to give crystals of the title compound, mp 275° C. and mass spectrum (m/e): 523(m+) and 505.

In the same manner but replacing glycyl-glycyl-glycyl-glycyl-glycyl-glycine with an equivalent amount of leucyl-glycyl-glycyl-glycine, valyl-threonyl-asparaginyl-glycyl-valine, phenylalanyl-leucyl-prolyl-glutaminyl-glycyl-methionine, isoleucyl-leucyl-tyrosyl-glycyl-tryptophyl-asparaginyl-glycine or glycyl-glycyl-valyl-phenylalanyl-prolyl-seryl-methionyl-alanine, the following compounds of formula I are obtained, respectively: cyclo[N-[1-(1-methylethyl)-2-cyclohexylamino-2-oxo-ethyl]-leucyl-glycyl-glycyl-glycyl], cyclo[N-[1-(1-methylethyl)-2-cyclohexylamino-2-oxo-ethyl]-valyl-threonyl-asparaginyl]-glycyl-valyl], cyclo[N-[1-(1-methylethyl)-2-cyclohexylamino-2-oxo-ethyl]-phenylalanyl-leucyl-prolyl-glutaminyl-glycyl-methionyl], cyclo[N-[1-(1-methyl-ethyl)-2-cyclohexylamino-2-oxo-ethyl]-isoleucyl-leucyl-tyrosyl-glycyl-tryptophyl-asparaginyl-glycyl] and cyclo[N-[1-(1-methylethyl)-2-cyclohexylamino-2-oxo-ethyl]-glycyl-glycyl-valyl-phenylalanyl-prolyl-seryl-methionyl-alanyl].

We claim:

1. A compound of formula I:

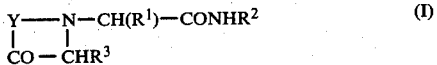   (I)

in which $R^1$ is lower alkyl; $R^2$ is lower alkyl or cyclo(lower)alkyl, $R^3$ is a neutral amino acid side chain selected from hydrogen or lower alkyl and Y is a peptide residue of the formula NHCH($R^4$)CO—NHCH($R^5$)CO—NHCH($R^6$)CO—NHCH($R^7$)CO—NHCH($R^8$)CO wherein $R^4$ is hydrogen, lower alkyl or benzyl; $R^5$, $R^6$ and $R^7$ each independently is hydrogen or lower alkyl and $R^8$ is hydrogen, lower alkyl or 2-(methylthio)ethyl.

2. A compound of formula I:

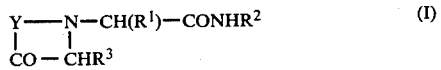   (I)

in which $R^1$ is lower alkyl; $R^2$ is cyclo(lower)alkyl, $R^3$ is a neutral amino acid side chain selected from hydrogen or lower alkyl and Y is a peptide residue of the formula NHCH($R^4$)CO—NHCH($R^5$)CO—NHCH($R^6$)CO—NHCH($R^7$)CO—NHCH($R^8$)CO wherein $R^4$ is hydrogen or benzyl; $R^5$, $R^6$ and $R^7$ each independently is hydrogen or lower alkyl and $R^8$ is hydrogen or 2-(methylthio)ethyl.

3. Cyclo[N-[1-(1-methylethyl)-2-cyclohexylamino-2-oxo-ethyl]-alanyl-phenyl-alanyl-valyl-glycyl-leucyl-methionyl], as claimed in claim 2 having a rotation of $[\alpha]_D^{25}$ −182° (c=1, dimethylformamide).

4. Cyclo[N-[1-(1-methylethyl)-2-cyclohexylamino-2-oxo-ethyl]-alanyl-phenyl-alanyl-valyl-glycyl-leucyl-methionyl], as claimed in claim 2 having a rotation of $[\alpha]_D^{25}$ −77° (c=1, dimethylformamide).

5. Cyclo[N-[1-(1-methylethyl)-2-cyclohexylamino-2-oxo-ethyl]-glycyl-glycyl-glycyl-glycyl-glycyl-glycyl], as claimed in claim 2.

6. A pharmaceutical composition comprising an antibacterial and antifungal amount of a compound of formula I, as claimed in claim 1, and a pharmaceutically acceptable carrier.

7. A method of treating bacterial and fungal infections in a mammal having said infections which comprises administering to said mammal an antibacterial and antifungal effective amount of formula I, as claimed in claim 1.

* * * * *